US009377392B2

(12) United States Patent
Rickards et al.

(10) Patent No.: US 9,377,392 B2
(45) Date of Patent: Jun. 28, 2016

(54) METHODS AND SYSTEMS FOR TESTING FLUIDS ON CRUSHED FORMATION MATERIALS UNDER CONDITIONS OF STRESS

(71) Applicant: PropTester, Inc., Cypress, TX (US)

(72) Inventors: Allan R. Rickards, Cypress, TX (US); Ian J. Renkes, Tomball, TX (US); David A. L. Garner, Tomball, TX (US)

(73) Assignee: PropTester, Inc., Cypress, TX (US)

( * ) Notice: Subject to any disclaimer, the term of this patent is extended or adjusted under 35 U.S.C. 154(b) by 392 days.

(21) Appl. No.: 14/019,059

(22) Filed: Sep. 5, 2013

(65) Prior Publication Data
US 2015/0059447 A1 Mar. 5, 2015

(51) Int. Cl.
*G01N 19/00* (2006.01)
*G01N 3/08* (2006.01)
*G01N 11/00* (2006.01)
*G01N 11/02* (2006.01)
*G01N 15/08* (2006.01)
G01N 33/28 (2006.01)

(52) U.S. Cl.
CPC ............... *G01N 19/00* (2013.01); *G01N 3/08* (2013.01); *G01N 11/00* (2013.01); *G01N 11/02* (2013.01); *G01N 15/08* (2013.01); G01N 33/28 (2013.01)

(58) Field of Classification Search
CPC ............................. G01N 19/00; G01N 33/28
See application file for complete search history.

(56) References Cited

U.S. PATENT DOCUMENTS

| 3,394,999 | A | | 7/1968 | Keith et al. |
| 4,016,932 | A | | 4/1977 | Kalfoglou |
| 4,192,382 | A | | 3/1980 | Schievelbein |
| 4,231,428 | A | * | 11/1980 | Needham ............. E21B 43/267 166/280.2 |
| 5,363,692 | A | | 11/1994 | Lafargue et al. |
| 8,286,514 | B2 | | 10/2012 | Anschutz et al. |
| 2008/0060444 | A1 | * | 3/2008 | Conway ................. G01N 3/08 73/821 |
| 2009/0306898 | A1 | * | 12/2009 | Anschutz ................ G01N 3/10 702/11 |
| 2011/0100113 | A1 | | 5/2011 | Anschutz et al. |
| 2013/0014946 | A1 | * | 1/2013 | Makarychev-Mikhailov C09K 8/62 166/280.2 |
| 2013/0067999 | A1 | | 3/2013 | Xu et al. |

OTHER PUBLICATIONS

ISO 13503-5, "Petroleum and Natural Gas Industries—Completion Fluids and Materials", International Standard, First Edition, 2006, 32 pgs.
Salehi et al., "Wettability Alternation of Carbonate Rock Mediated by Biosurfactant Produced From High-Starch Agricultural Effluents", 9th International Symposium on Evaluation of Wettability and Its Effect on Oil Recovery, Sep. 2006, 12 pgs.
(Continued)

*Primary Examiner* — Hezron E Williams
*Assistant Examiner* — David Z Huang
(74) *Attorney, Agent, or Firm* — Egan, Peterman, Enders & Huston LLP.

(57) ABSTRACT

Methods and systems that may be employed to dynamically test the effect of fluids (e.g., well treatment chemicals such as well stimulation treatment chemicals, enhanced oil recovery "EOR" chemicals, etc.) on hydrocarbon recovery from crushed reservoir formation materials under conditions of applied stress. The disclosed methods and systems may be used in one embodiment to dynamically test types of low permeability formations (e.g., such as shale, limestone, quarried rock, etc.).

28 Claims, 6 Drawing Sheets

(56) References Cited

OTHER PUBLICATIONS

Gall, "Laboratory Feasibility Study of ASP Systems for the Karamay Reservoir", Phase 2 Oil Recovery Evaluations, Apr. 1995, 70 pgs.

CRS Proppants, "Unconfined Compressive Strength (USC) Testing", 2012, 2 pgs.

ASTM D2166-06, "Standard Test Method for Unconfined Compressive Strength of Cohesive Soil", Printed From Internet Aug. 28, 2013, 4 pgs.

* cited by examiner

METHODS AND SYSTEMS FOR TESTING FLUIDS ON CRUSHED FORMATION MATERIALS UNDER CONDITIONS OF STRESS

FIELD OF THE INVENTION

This invention relates generally to methods and systems for testing formation materials.

BACKGROUND

Hydrocarbon production from shale formations is accomplished through natural formation fractures that are in communication with the producing wellbore. Stimulation treatments, such as hydraulic fracturing, are often performed on shale formation completions to enhance productivity. These stimulation treatments typically include surface active agents and other chemicals that interact with the formation and in situ formation fluids to enhance the flow and production of hydrocarbons.

In the past, core flow permeameters have been used to dynamically evaluate the interaction of oil and chemical treatments. For example, formation permeability to fluids has been measured by flowing brine, hydrocarbon or nitrogen representing different fluid phases through a whole solid core sample taken from a permeable formation such as sandstone. Different chemical treatments are applied to the formation core, and the resulting permeability measured and compared. However, permeameters are ineffective in evaluating core samples of impermeable oily shale. Static bottle tests have also been used to evaluate the interaction of oil and chemical treatments on formations but cannot distinguish between chemicals effective in aiding the production of hydrocarbons from chemicals that can slow hydrocarbon production by decreasing the interaction between the hydrocarbon, formation and natural formation brine. In such static tests hydrocarbon and chemical treatments are mixed, with or without shale or other formation material, and the resulting reaction of the oil is observed. Such static tests induce no fluid flow through the formation materials and therefore do not achieve the same accuracy as dynamic tests.

In the past, unconfined compressive strength (UCS) cells have been used to measure the strength of resin coated sand samples. A UCS cell includes a solid movable piston mounted within a cylinder that separates a test cell cavity from a closed pressure application cavity. A pressure port is provided on a first end of the cylinder to allow injection of pressurized fluid into the closed pressure cavity to cause the piston to move toward the test sample cavity and thus apply compressive stress to a resin coated sand sample that has been placed into the test sample cavity. A fluid outlet is provided on an opposing second end of the cylinder to allow fluids to exit from the test sample cavity while pressure is increased within the pressure cavity. The test cavity has no fluid inlet, and during typical resin coated sand testing operations, once the pressure cavity is pressured up the fluid outlet of the test cavity is closed off for the duration of the test.

SUMMARY OF THE INVENTION

Disclosed herein are methods and systems that may be employed to dynamically test the effect of fluids on hydrocarbon recovery from crushed reservoir formation materials under conditions of applied stress, e.g., such as an applied stress substantially equivalent to the in situ overburden stress corresponding to the reservoir conditions for the tested formation material. Advantageously, the disclosed methods and systems may be used in one embodiment to dynamically test types of low permeability formations (e.g., such as shale, limestone, quarried rock, etc.) that do not have sufficient permeability to allow use of conventional uncrushed formation dynamic testing methods, such as core flow permeameters. Using the disclosed methods and systems, a wide variety of chemicals and other fluids may be tested in undiluted or diluted form (e.g., tested liquids may be diluted in aqueous solvent such as potassium chloride or sodium chloride brines, ammonium chloride, calcium chloride, combinations thereof, etc. or other suitable solvent), or in undiluted form (e.g., such as undiluted alkali surfactant polymer). In one exemplary embodiment, a liquid chemical sample of interest may be diluted only with a water based solvent, and not diluted with any hydrocarbon-based solvent.

Examples of classes and particular types of chemicals that may be tested include, but are not limited to, liquid well treatment chemicals such as well stimulation treatment chemicals, enhanced oil recovery "EOR" and polymer flood chemicals, demulsifiers, surface tension reducers, surface active agents, fluorosurfactants, alkali surfactant polymers, etc. Specific examples of such chemicals include, but are not limited to, polyethylene glycol monohexyl ether, surfactant blends such as poly(oxy-1-2-ethanediyl)alpha(4-nonylphenyl)-omega-hydroxy-branched, naphthalene, 1,2,4 trimethylbenzene blended with naphtha and alcohol, and mixtures such as ethoxylated alcohols and methyl alcohol or N-Methyl Pyrrolidone and D-limonene, etc. The effect of such chemicals on hydrocarbon recovery from particular crushed reservoir formation materials may also be evaluated and quantitatively or qualitatively compared to each other, e.g., under similar conditions.

For example, the disclosed methods and systems may be implemented to so test crushed reservoir formation materials sampled from low permeability formations (e.g., having a matrix absolute permeability of less than or equal to about 1 millidarcies (md), alternatively having a matrix absolute permeability of from about 0.001 md to about 1 md, and further alternatively having a matrix absolute permeability of from about 0.01 md to about 1 md. Examples of such low permeability formation materials include, but are not limited to, shale and limestone formations that are typically produced using hydraulically fractured well completions. However, it will be understood that crushed materials from formations having a matrix absolute permeability greater than about 1 md or less than about 0.001 md may also be tested. Thus, the disclosed methods and systems also make it possible to evaluate the effectiveness of chemical treatment fluids on such crushed low permeability formation materials and other formation materials under conditions of applied stress and optionally at elevated temperatures. In one embodiment, the disclosed methods and systems may be further employed to dynamically test the effect of chemicals on hydrocarbon recovery from crushed reservoir material at combined reservoir conditions of formation stress, formation temperature, and/or formation fluid or pore pressure.

In one exemplary embodiment, the disclosed methods and systems may be employed to test the effectiveness of surface active agents and/or other well treatment chemicals (e.g., such as may be employed during hydraulic fracturing) for their ability to interact with reservoir formation materials and in situ hydrocarbons to increase or otherwise enhance the flow and production of hydrocarbons (e.g., oil and/or gas) from the formation into a completed wellbore. In this regard, the pore space in crushed formation material may be saturated with a formation hydrocarbon such as oil, and various chemical treatment fluids may then be evaluated by flowing fluids through the crushed formation material under actual conditions of formation stress, downhole formation temperature, and/or formation pore pressure to determine effect of the different chemicals on hydrocarbon production. Chemical treatment fluids containing different chemicals, such as different types of surface active agents, may be tested and graded for efficiency by measuring the amount of production of the oil phase from the crushed formation material relative to the produced aqueous phase from an aqueous-based displacement fluid.

The disclosed methods and systems may be implemented in one embodiment using any test equipment configuration suitable for applying stress to crushed formation materials while simultaneously inducing flow of tested chemical treatment fluid/s and other fluid/s as test solution/s through the crushed formation materials to test the effect of the tested fluid/s on the production of hydrocarbons from the formation material. Examples of suitable test equipment configurations include, but are not limited to, International Organization for Standardization (ISO) 13503-5 conductivity press and conductivity cells or an unconfined compressive strength (UCS) cell modified with a flow through piston. In one exemplary embodiment, production of hydrocarbons may be measured by flowing chemical treatment fluids followed by suitable water-based or other liquid displacement fluids through crushed formation materials that have been previously saturated with hydrocarbons, such as formation oil. Volume or relative percentage of hydrocarbon recovered from the crushed formation material under test during water displacement may be measured using any suitable measurement apparatus including, but not limited to, a volumetric separator configured to provide suitable residence time to allow separation of the recovered hydrocarbons from water-based effluent.

In one respect, disclosed herein is a method, including: substantially saturating the pore spaces of a crushed formation sample with hydrocarbon; applying a compressional stress to the saturated crushed formation sample; flowing a test solution through the crushed formation sample while the crushed formation sample is subjected to the applied compressional stress to produce an effluent from the crushed formation sample; and determining the amount of hydrocarbon recovered from the effluent produced from the crushed formation sample while the crushed formation sample is subjected to the applied compressional stress.

In another respect, disclosed herein is a test system, including: a system body having a test cavity defined therein that contains a crushed formation sample that is substantially saturated with hydrocarbon; at least one fluid inlet in fluid communication with the test cavity and configured to receive a test solution to induce a flow of fluid through the crushed formation sample to produce an effluent; at least one fluid outlet in fluid communication with the test cavity and configured to receive the effluent from the crushed formation sample; and at least one stress application member configured to apply compressive stress to the saturated sample of crushed formation material contained within the test cavity at the same time that fluid flow is induced through the crushed formation sample from the fluid inlet to the fluid outlet of the test cavity. A fluid seal is formed around the crushed formation sample within the test cavity to substantially contain pressurized fluid flow through the crushed formation sample from the fluid inlet to the fluid outlet.

In another respect, disclosed herein is a test system, including: a system body having a test cavity defined within a first end of the system body and a closed pressure application cavity defined within a second end of the system body, the test cavity being sealed from the closed pressure application cavity such that an internal volume of the test cavity has substantially no fluid communication with an internal volume of the closed pressure application cavity, and the test cavity being configured to receive a crushed formation sample therein; a movable piston sealingly received within the system body between the first and second ends of the system body, the movable piston being movable between the first and second ends of the system body while at the same time maintaining a fluid seal between the test cavity and the closed pressure application cavity; a movable inlet fluid conduit extending from outside the second end of the system body through the closed pressure application cavity and through an opening defined in the movable piston, the inlet fluid conduit forming a fluid seal with the system body and having substantially no fluid communication with the closed pressure application cavity; at least one system fluid inlet in fluid communication with the inlet fluid conduit such that the system fluid inlet is in fluid communication with the test cavity, the system fluid inlet and test fluid conduit being configured to receive a first injected fluid to induce a flow of fluid through the crushed formation sample to produce an effluent; at least one pressure application fluid inlet in communication with the closed pressure application cavity and configured to receive a pressure application fluid that is injected into the closed pressure application cavity to cause an increase in fluid pressure differential across the movable piston between the closed pressure application cavity and the test cavity; and at least one fluid outlet in fluid communication with the test cavity and configured to receive the effluent from the crushed formation sample. The movable piston may be configured to respond to an increase in fluid pressure differential between the closed pressure application cavity and the test cavity by applying compressive stress to the crushed formation material contained within the test cavity at the same time that injection of the first fluid induces fluid flow through the crushed formation sample from the system fluid inlet to the fluid outlet of the test cavity.

DESCRIPTION OF ILLUSTRATIVE EMBODIMENTS

Figure 1A:
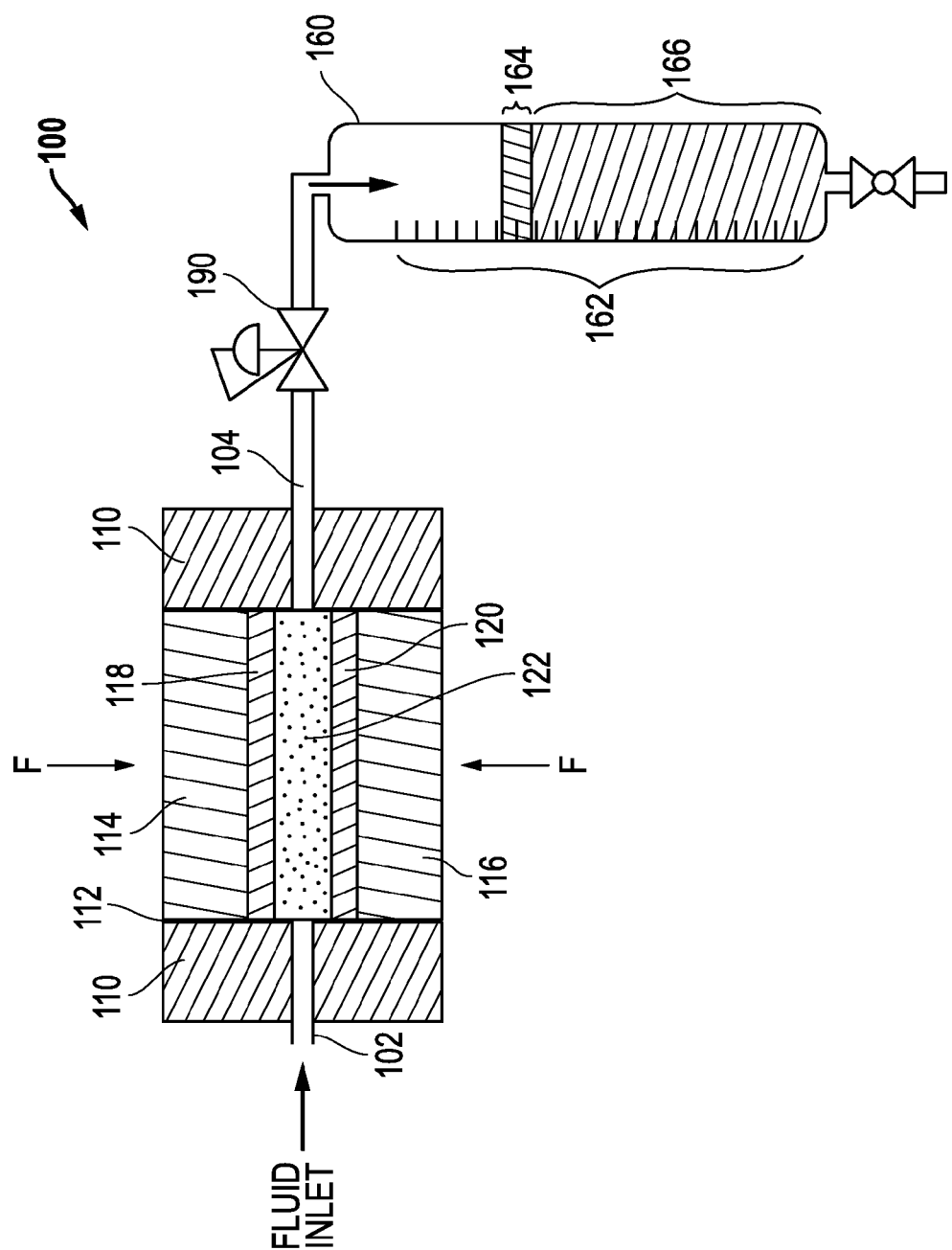
FIG. 1A illustrates a cross-sectional view of a crushed formation testing system according to one exemplary embodiment of the disclosed methods and systems.
Figure 1B:
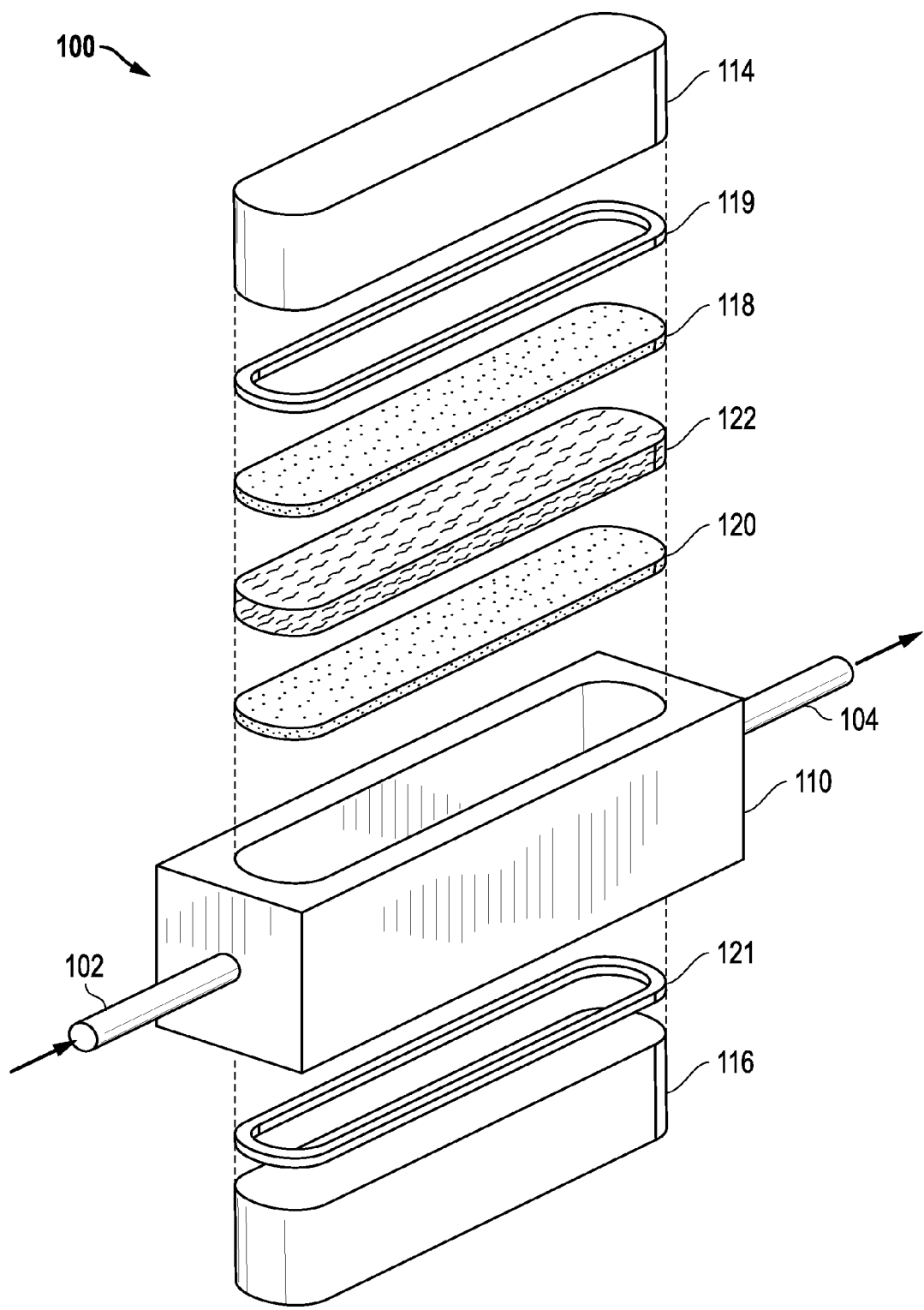
FIG. 1B illustrates an exploded overhead perspective view of selected components of a crushed formation testing system according to one exemplary embodiment of the disclosed methods and systems.

FIG. 1A illustrates a cross-sectional view of a crushed formation testing system 100 according to one exemplary embodiment of the disclosed methods and systems. As shown, system 100 includes a flow-through test cell body 110 having test cell cavity 112 defined therein. A fluid inlet 102 for injection of various fluids (e.g., solutions of liquids such as water, liquid chemicals, liquid hydrocarbons, combinations thereof, etc.) into the test cell cavity (e.g., by a positive displacement pump) and a fluid outlet 104 that is coupled to output the injected fluids after passage through the test cell body 110. A particle filter (e.g., 100 mesh screen) may be provided at the fluid outlet 104 to contain particles of the crushed sample within the test cell cavity 112 during flow testing. A crushed formation sample 122 (e.g., such as a sample of crushed shale or other low permeability formation) is sandwiched or otherwise positioned within test cell cavity 112 between stress application members in the form of pistons 114 and 116 in this exemplary embodiment that move toward each other so as to cooperatively provide an inward compression force to crushed formation sample 122 in the direction of the arrows. In this embodiment, optional compression dies 118 and 120 are provided between the crushed formation sample 122 and respective pistons 114 and 116 as shown. Compression dies 118 and 120 may be of any suitable material (e.g., uncrushed Ohio sandstone, stainless steel metal plates, berea sandstone, formation cores, limestone or dolomite, etc.) for containing crushed formation sample 122 between pistons 114 and 116 under conditions of applied stress induced by the applied compressive force of pistons 114 and 116 during testing, while at the same time transmitting the applied compressive stress to the sample 122. Compressive forces in the direction of the arrows may be applied to pistons 114 and 116 in any suitable manner, e.g., using a force-inducing apparatus such as pressure-controllable conductivity press, hydraulic press, manual hydraulic press, etc. FIG. 1B illustrates an exploded overhead perspective view of selected components of crushed formation testing system 100.

As further shown in the cross-sectional view of FIG. 1A, crushed formation sample 122 is sealingly positioned in line between fluid inlet 102 and fluid outlet 104 to allow for flow of injected fluids from fluid inlet 102 to fluid outlet 104 at the same time that compressive stress is applied to sample 122 by pistons 114 and 116 during testing. Flow rate may be optionally controlled in one embodiment such that fluid flow through crushed formation sample 122 is not turbulent, e.g., the flow rate through test cell body 110 and cavity 112 may be limited to achieve Darcy or non-turbulent flow rates (e.g., plug flow rate, laminar flow rate) through the crushed formation sample 122 during testing to avoid interference with hydrocarbon production from a formation sample during flow testing, although turbulent flow through sample 122 may also be present during testing in other embodiments. It will be understood that Darcy or non-turbulent flow rate will vary based on the particular dimensions of a given test cell cavity employed and/or characteristics of a particular crushed formation sample and pack width under test. In this regard, it will be understood that the disclosed methods and systems may be employed with conductivity test cells of various sizes, with examples of possible cross sectional flow area dimensions for a conductivity test cell cavity 112 including, but are not limited to, 10 $in^2$, 25 $in^2$, 100 $in^2$, etc.

In one embodiment, the amount of applied compressive stress may be controlled (e.g., by controlling hydraulic press pressure on pistons 114 and 116) and the amount of fluid injection pressure may be controlled (e.g., by back pressure valves, chokes, variable injection pump speed, etc.). An optional heating element/s (e.g., electrical heating elements) may be provided for heating the test cell body 110, test cell cavity 112 and its contents to a desired temperature during temperature. In this way, a desired combination of compressive stress, temperature, and fluid pressure may be applied to a crushed formation sample 122 during testing, e.g., so as to substantially simulate in situ reservoir conditions of overburden pressure, static formation temperature, and/or reservoir pore pressure for the formation from which sample 122 has been taken.

In this regard, any suitable compressive force may be applied during testing, and may in one embodiment be substantially equal to the in situ reservoir overburden pressure of the formation from which sample 122 has been taken. In one exemplary embodiment, a compressive stress applied to sample 122 during testing may be from greater than 0 psi up to about 500 psi, alternatively from greater than 0 psi up to about 20,000 psi, alternatively from about 500 psi to about 20,000 psi, alternatively from about 500 psi to about 5000 psi, alternatively from about 500 psi to about 2000 psi, alternatively from about 500 psi to about 1000 psi, alternatively from about 250 psi to about 20,000 psi, alternatively from about 250 psi to about 5000 psi, alternatively from about 250 psi to about 2000 psi, alternatively from about 250 psi to about 1000 psi, alternatively from about 250 psi to about 500 psi, alternatively from about 50 psi to about 20,000 psi, alternatively from about 50 psi to about 5000 psi, alternatively from about 50 psi to about 2000 psi, alternatively from about 50 psi to about 1000 psi, alternatively from about 50 psi to about 250 psi, and alternatively from about 50 psi to about 500 psi. However, it will be understood that compressive stresses greater than about 20,000 psi and less than about 50 psi may also be employed.

Injected fluid pressure (e.g., test solution pressure) may be controlled in one exemplary embodiment using a combination of the pressure of fluid supplied to fluid inlet 102 and back pressure applied to fluid exiting out fluid outlet 104, e.g., using an optional back pressure valve 190 provided on outlet 104 or other suitable back pressure technique and/or apparatus. For example, a fluid pressure of flowing fluid within test cavity 112 during solution testing may be controlled to be from about 200 psi to about 1000 psi, although pressures less than about 200 psi and greater than about 1000 psi may be alternatively employed. Fluids introduced through fluid inlet 102 and/or test cell body 110 itself may be optionally heated using during testing using any suitable heating apparatus, such as heat exchanger, electrical heating element/s, etc. In one exemplary embodiment, such heating may be employed to achieve a fluid and/or formation sample temperature of from about 50° C. to about 225° C. during testing, although temperatures less than about 50° C. and greater than about 225° C. may be alternatively employed.

As further shown in FIG. 1B, optional elastomeric seals 119 and 121 (shown in FIG. 1B) such as Tetraseal® sealing ring may be provided (e.g., between piston 114 and compression die 118 and between piston 116 and compression die 120), or alternatively any other suitable sealing arrangement may be employed, to form a fluid seal against the interior walls of test cavity 112 to contain injected fluids under pressure and test solution fluid flow within test cavity 112 during testing. Suitable pressure ports may be provided in fluid communication with fluid inlet 102, fluid outlet 104 and/or test cavity 112 for measuring fluid pressure at one or more points within the test cavity 112, and/or the differential pressure between the fluid inlet and fluid outlet during fluid flow through the crushed formation sample 122 during testing.

As shown, system 100 may also include an optional volumetric separator vessel 160 that is coupled to receive the output fluids from fluid outlet 104 of flow-through cell body 110. In this embodiment, separator vessel 160 may be a transparent (e.g., glass) vessel as shown which is provided with graduations 162 to allow for measurement of volumes of different fluids (e.g., hydrocarbon 164 and water-based fluids 166) received from outlet 104 of test cell body 110 during dynamic testing. In one exemplary embodiment, volumetric separator 160 may be constructed of a cylindrical graduated funnel going to a round bottom flask feeding into an Erlenmeyer flask, and may be used to separate and measure hydrocarbon and water effluent received from test cell body 110.

Figure 1C:
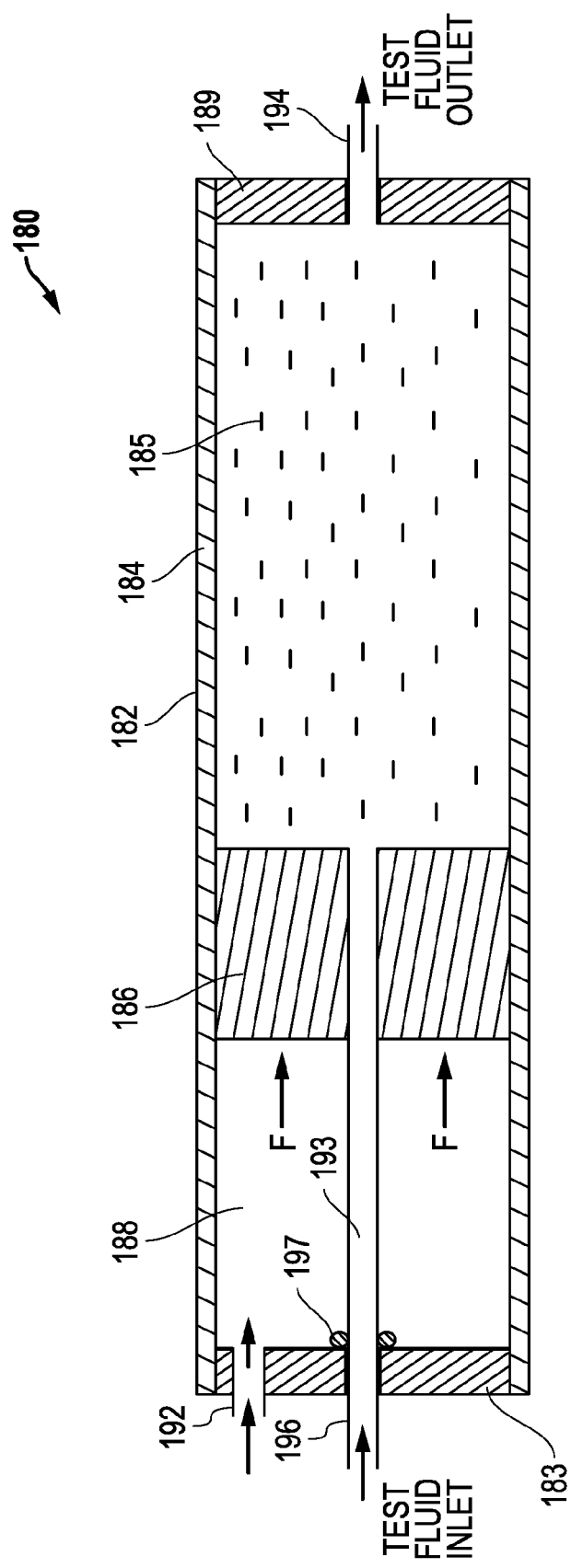
FIG. 1C illustrates a cross-sectional view of a crushed formation testing system according to one exemplary embodiment of the disclosed methods and systems.

In the exemplary system embodiment of FIG. 1A, flow-through test cell body 110 is configured as a stainless steel International Organization for Standardization (ISO) conductivity cell with stainless steel pistons 114 and 116, one example of which is described in U.S. Pat. No. 8,286,514, which is incorporated herein by reference in its entirety. However, it will be understood that the illustrated test cell embodiment of FIG. 1A is exemplary only, and that any other system and test cell configuration may be employed that is suitable for using one or more pistons or other suitable compressive stress application members to apply compressive stress to a sample of crushed formation material contained within the test cell at the same time that fluid flow is induced through the contained sample within the test cell. In this regard, it is possible that compressive force may be applied to a crushed formation sample from only one direction or from more than two opposing directions (e.g., including extending radially inward from around the perimeter of a crushed formation sample), rather than from the two opposing directions as illustrated in FIG. 1A. Examples of other types of test cells that may be employed to contain and test a crushed formation sample by flowing fluids through the crushed sample under conditions of applied compressive stress include, but are not limited to, modified unconfined compressive strength (UCS) cell as illustrated in FIG. 1C. It will also be understood that volume or relative volume of different fluids received from a test cell during testing may be measured using any other suitable fluid measurement apparatus and/or technique, e.g., by measuring one or more effluent properties such as using measurements of effluent capacitance, effluent light spectra (spectroscopy), effluent density, etc.

FIG. 1C illustrates a side cross-sectional view of one alternative embodiment of a test system 180 having a flow-through test cell body 182 that may be employed in one exemplary embodiment to dynamically test the effect of fluids on hydrocarbon recovery from crushed reservoir formation materials under conditions of applied stress. In one embodiment, the flow-through test cell body may be provided as a cylindrical stainless steel tube 182, e.g., such as a stainless steel cylinder with 2000 psi pressure rating having an internal diameter of 1 inch and a length of from about 12 inches to about 13 inches long. However, it will be understood that greater or lesser lengths, greater or lesser internal diameters, and/or cross-sectional shapes other than cylindrical (e.g., such as square, rectangular, oval, etc.) may be employed in other embodiments. In this embodiment, the internal volume of test system 180 is divided by a movable flow-through piston 186 into a test cell cavity 184 and a closed pressure application cavity 188 that are each defined within walls of test cell body 182. The test cell cavity 184 is defined between the movable piston 186 and a first stationary end cap 189 sealingly provided on one end of test cell body 180, and the closed pressure application cavity 188 is defined between the movable piston 186 and a second stationary end cap 183 sealingly provided on a second and opposite end of test cell body 180. Movable piston 186 may be sized and machined with outer dimensions complementary to the interior dimensions of test cell body 182 such that piston 186 forms a slidable metal to metal fluid seal against the interior walls of test cell body 182.

In one exemplary embodiment, optional metal sealing rings, packing, elastomeric sealing elements, etc. may be provided on the outer diameter of piston 186 to form a fluid seal with the interior surfaces of test cell body 182 such that there is substantially no fluid communication between test cell cavity 184 and pressure application cavity 188. As further shown in FIG. 1C, a system fluid inlet 196 (e.g., such as ⅛ or ¼ inch ID stainless steel tubing) is provided for injection of various fluids (e.g., water, chemicals, hydrocarbons, etc.) into the test cell cavity 184 (e.g., by a positive displacement pump) via an internal movable inlet fluid conduit 193 that extends through an opening defined in piston 186 and that is capable of moving relative to stationary end cap 183 while at the same time allowing movement of movable piston 186 within interior dimensions of test cell body 182, e.g., in response to force on piston 186 in the direction of the arrows. A fluid outlet 194 (e.g., such as ¼ inch stainless steel tubing) is coupled to output the injected fluids after passage through the test cell body 180, e.g., to a volumetric separator vessel 160 as illustrated in FIG. 1A or other suitable fluid measurement apparatus. A particle filter (e.g., 100 mesh screen) may be provided at the fluid outlet 194 to contain particles of the crushed sample within the test cell cavity 184 during flow testing.

Still referring to FIG. 1C, a pressure application fluid inlet 192 (e.g., such as ¼ inch ID stainless steel tubing) is provided for purposes of injecting nitrogen, water, hydraulic oil, etc. under pressure (e.g., using a positive displacement pump) so as to increase the pressure in closed pressure application cavity 188 relative to cavity 184. This fluid pressure differential applies force on piston 186 in the direction of the arrows, which in turn causes moveable piston 186 to put compressive stress on crushed reservoir formation materials 185 sealingly contained within cavity 184. The fluid pressure applied to closed pressure application cavity 188 may be maintained while test fluids are injected through test system fluid inlet 196 and movable inlet fluid conduit 193 (e.g., such as ⅛ or ¼ inch ID stainless steel tubing) to cause flow of injected test fluids across test cavity 184 and contained sample 185 and out outlet 194 at the same time that compressive stress is applied to sample 185 by movable piston 186 during testing. As shown, one or more O-rings 197 may be provided to form a fluid seal between the second stationary end cap 183 and movable inlet fluid conduit 193 during operation, thus forming a fluid seal between movable inlet fluid conduit 193 and stationary end cap 183 that substantially contains fluid pressure within cavity 188 during testing and movement of inlet fluid conduit 193 to help maintain a steady compressive stress on the formation sample 185. It will be understood that in one exemplary embodiment, stationary end caps 192 and 194 may be removable (e.g., threaded onto or into test cell walls 182) such that crushed formation material 185 may be inserted into the test cell body 180 for testing and removed after testing. It will be understood that the particular dimensions and component materials described above for test cell body 180 of FIG. 1C are exemplary only, and that other suitable dimensions and materials may be employed.

Figure 2:
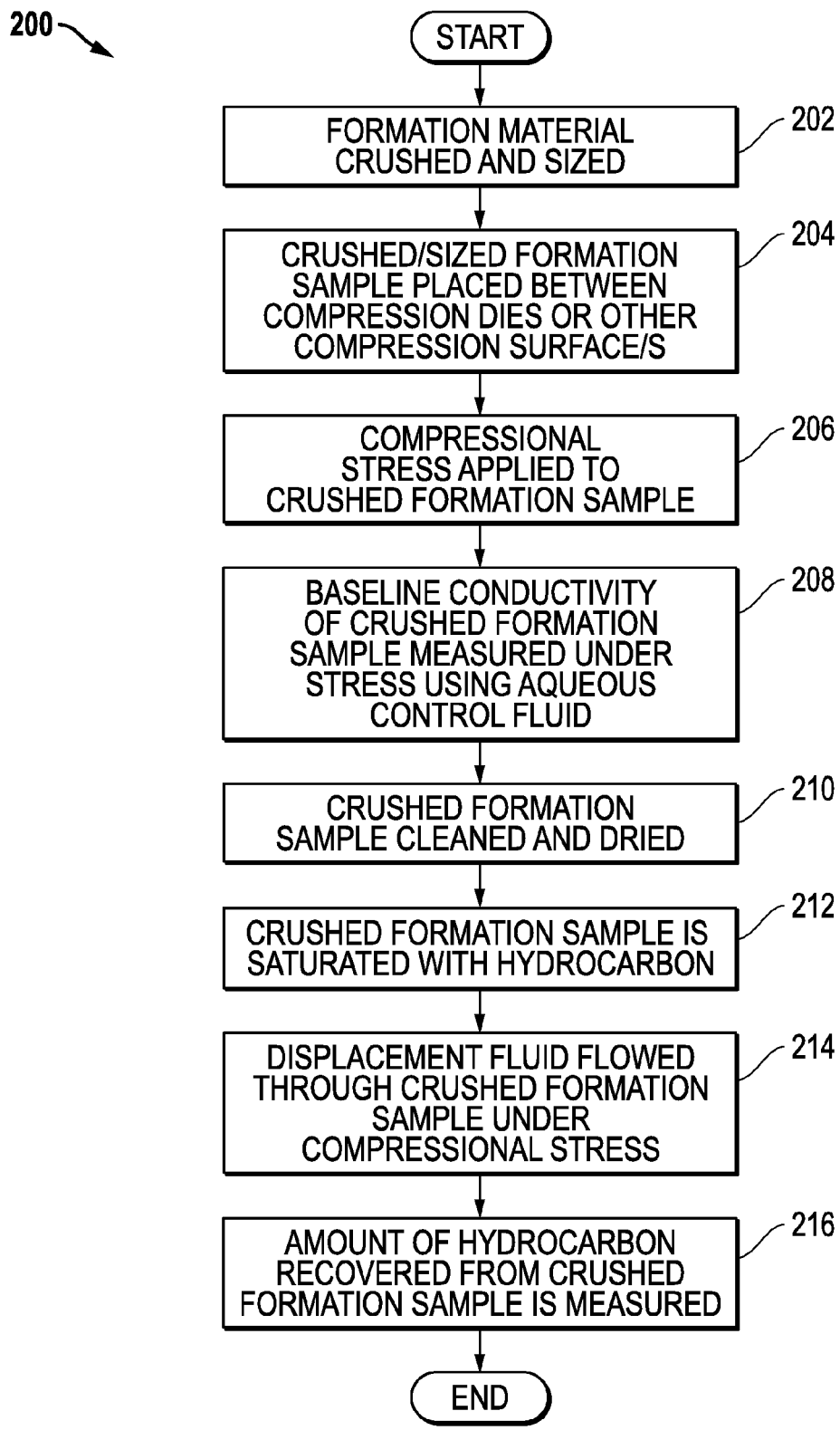
FIG. 2 illustrates a methodology that may be performed for testing well treatment chemicals on crushed formation material under conditions of applied stress according to one exemplary embodiment of the disclosed methods and systems.

In one embodiment using the disclosed methods and systems, the effect and/or efficiency of well treatment chemicals, such as surface active agents, may be tested on crushed formation material under applied stress in any suitable manner. FIG. 2 illustrates one exemplary embodiment of a methodology 200 that may be performed for testing the well treatment chemicals on crushed formation material under conditions of applied stress using the exemplary crushed formation testing system embodiment of FIG. 1A. As shown, methodology 200 may begin in step 202 by crushing and sizing a formation material sample 122 such as shale or other low permeability formation material of interest. The formation material may be obtained from a downhole sample or other suitable source and may be sized as desired, for example, to −30+200 mesh US Standard sieve or other desired larger or smaller size and/or size distribution. It will be understood that a formation may be crushed to any size (e.g., using a roll mill) that is suitable for measuring testing the effect of chemical/s on hydrocarbon recovery from crushed reservoir formation materials under stress, and may in one embodiment be selected based on particular characteristics (e.g., permeability) of the reservoir formation material.

Next, in step 204, the crushed and sized formation sample may be placed in test cell cavity 112 between compression dies 118 and 120, although it will be understood that any other suitable configuration of flow-through cell having suitable compression surface/s for applying compression stress to a crushed formation sample may be employed. Where compression dies 118 and 120 are porous materials (e.g., such as Ohio sandstone wafers), the dies 118 and 120 may be substantially saturated in hydrocarbon (e.g., liquid hydrocarbon under preparation and test conditions such as formation condensate, formation oil, Exxon Isopar isoparaffinic fluids, naphtha or other solvents, etc.) or other non-compressible pore-space filling liquid (e.g., such as brine) by vacuum saturation or other suitable technique prior to placement of the formation sample 122 between dies 118 and 120 within test cell cavity 112. This initial hydrocarbon saturation step may be performed to displace gas and prevent loss of injected oil into the porous dies 118 and 120 during later flow of oil through formation sample 122, and may be omitted where non-porous compression dies 118 and 120 are used.

Once appropriately sized and placed in test cell cavity 112 between the compression dies 118 and 120, the conductivity of the sized formation material sample 122 may be optionally measured in step 208 by flowing an aqueous control fluid such as 2% potassium chloride water though crushed formation sample 122 by injecting the aqueous control fluid into fluid inlet 102 of the test cell cavity 112 while the crushed formation sample 122 is subjected to a desired applied compressional stress that has been applied by pistons 114 and 116 or other compression surfaces in step 206. This baseline conductivity measurement may be done for purposes of comparison to the measured conductivity of other formation test samples 122, and may be performed using ISO 13503-5 standard testing procedures or any other suitable conductivity measurement technique. After the baseline conductivity measurement of step 208, the formation sample 122 may then be cleaned in step 210, e.g., by flushing the sample 122 with deionized water to remove any residual salt from formation sample 122 and then dried with hot nitrogen to remove remaining water.

Once the formation sample 122 has been dried, hydrocarbon (e.g., liquid hydrocarbon under preparation and test conditions such as formation condensate, formation oil, brine, Isopar, naphtha or other solvents, etc.) may then be vacuum saturated or otherwise injected (e.g., by pumping under pressure) into fluid inlet 102 of the test cell cavity 112 to displace gas from the sample and until formation sample 122 is substantially oil saturated in step 212, and the amount of oil required to achieve this substantial oil saturation may be measured and recorded for purposes of comparison to flow tests on other crushed formation samples 122. Vacuum saturation may be performed, for example, by substantially evacuating test cavity 112 and allowing hydrocarbon to be draw in through inlet 102 and/or outlet 104 until saturation of sample 122 is achieved. The formation sample 122 is now ready for testing with a desired displacement fluid/s in step 214. To establish an optional baseline for comparison to other tested formation samples 122, an aqueous-based control displacement fluid (such as 2% potassium chloride water) may be mixed and flowed through the crushed formation sample 122 by injection into fluid inlet 102 of the test cell body 110 while the formation sample 122 within test cell cavity 112 is subjected to a desired applied compressional stress that is applied by pistons 114 and 116. The effluent may be collected in volumetric separator vessel 160 at the outlet 104 of the cell body 110, and a baseline volume of recovered oil that is displaced from the formation sample 122 by the control fluid may be measured in step 216 after it has separated from the aqueous phase in the separator vessel 160.

The above procedure of FIG. 2 may be repeated in a similar manner to test one or more selected chemicals (e.g., well treatment chemical/s such as surface active agents) that may be optionally mixed with a light brine or 2% KCl water to form a chemical treatment fluid that is then flowed as per step 214 through a respective crushed formation sample 122 within test cell cavity 112 under applied compressional stress to the separator vessel 160, and the amount of oil recovered in separator 160 measured as per step 216 in a manner similar to the control fluid run for each crushed formation sample 122. The above procedure of FIG. 2 may be repeated on a separate crushed formation sample 122 from the same formation material for each of multiple different chemical treatment fluids, and the measured amount of recovered oil produced from flow of each chemical treatment fluid run through a treated formation sample 122 may then be compared to the amount of recovered oil produced from flow of the control fluid with no other chemicals added through an untreated formation sample 122, e.g., to determine if interaction of a given injected chemical treatment fluid with the oil saturated formation sample 122 acts to increase or decrease the amount of recovered oil relative to the injected control fluid and/or relative to other types of chemical treatment fluids. For example, oil recovery effectiveness of surface active agents that have low surface tension but high contact angle (and that may in one embodiment act to increase oil production) may be differentiated from oil recover effectiveness of other surface active agents that have low surface tension and low contact angle (and that may in one embodiment act to hinder oil production).

It will be understood that the above-described methodology 200 of FIG. 2 is exemplary only, and that any other combination of additional, fewer, and/or alternative steps may be employed that is suitable for testing the effect and/or efficiency of well treatment chemicals or other fluids on a crushed formation sample under conditions of applied compressional stress. For example, it will be understood that one or more chemicals or other fluids may be first applied to the crushed formation sample 122 prior to placement of the sample 122 between the compression dies 118 and 120 within test cell cavity 112, after which a chosen displacement fluid (e.g., control fluid or chemical treatment fluid) may then be flowed through the sample 122 in test cell cavity 112.

EXAMPLES

The following examples are illustrative only, and are not to be construed as limiting the scope of the disclosed methods and systems, or claims thereto.

The effectiveness of various different surfactant chemicals on enhancing oil production from crushed Eagleford shale formation samples was dynamically evaluated at simulated down hole reservoir conditions of applied stress and elevated temperature using a single ISO 10 in$^2$ cross sectional area conductivity cell setup, i.e., having cell length of approximately 7 inches and a cell width of approximately 1.5 inches. Each formation sample was tested on the same conductivity press and using the same temperature and stress. A volumetric separator was coupled to the output of the test cell body of the conductivity cell, and was constructed of a cylindrical graduated funnel going to a round bottom flask feeding into an Erlenmeyer flask.

For the testing, a sample of Eagleford formation core was crushed to a US mesh of −30+100 US Standard sieve and split into equal representative samples of 126 grams and 81 cubic centimeters, and the sieve distribution and median particle diameter measured. Produced oil from the Eagleford shale formation was filtered to remove organic portions such as paraffin and asphaltenes. For each crushed formation sample test run, two Ohio sandstone compression die wafers were vacuum saturated in the filtered Eagleford formation oil. Each crushed formation sample was then placed between the two oil saturated Ohio sandstone wafers, loaded at 4 lbs/ft$_2$ (for a tested formation sample pack width of about 0.5 inches) into the test cell cavity of the ISO conductivity cell, and heated to 87° C. For each sample, the conductivity stack and crushed formation sample was initially stressed to 250 psi for 12-24 hours using the conductivity press. Although a particular sample loading of 4 lb/ft$^2$ was used for the testing in this example, it will be understood that other sample loading values (e.g., sample loading values from about 2 lb/ft$^2$ to about 4 lb/ft$^2$, or sample loadings greater than about 2 lb/ft$^2$ or less than about 4 lb/ft$^2$), as well as different tested formation sample sample pack widths (e.g., widths from about 0.25 inches to about 0.5 inches, or widths greater than about 0.5 inches or less than about 0.25 inches) may be alternatively employed as needed or desired to fit different test applications and/or different formation types.

Next, baseline conductivity was established for each crushed formation sample by injecting filtered 2% potassium chloride water while subjecting the crushed formation sample to an applied stress of 500 psi at 87° C. Injected solution flow rates of 2 milliliter per minute were used for all phases of the testing to maintain Darcy or non-turbulent flow through the conductivity cell. This baseline conductivity value was compared to the baseline conductivity of each of the other tested crushed formation samples to ensure that each different test run was performed on a crushed formation sample having substantially the same conductivity. For the testing of the Examples herein, International Standards Organization (ISO) procedures 13503-5:2006E entitled "Procedures for Measuring the Long Term Conductivity of Proppants" was used to determine conductivity and permeability values from the test results according to the following relationships (it being understood that any other suitable methodology and/or relationships for determining conductivity and/or permeability may be alternatively employed in the practice of the disclosed methods and systems):

Conductivity: $kWf=26.78(\mu Q/\Delta P)$

Permeability: $k=321.4\mu Q/[(\Delta P)Wf]$ where:

k is the tested formation sample pack permeability, expressed in Darcy's;

kWf is the tested formation sample pack conductivity, expressed in millidarcy-feet;

μ is the viscosity of the test liquid at test temperature, expressed in centipoises;

Q is the flowrate, expressed in cubic centimeters per minute;

ΔP is the differential pressure, expressed in psi; and

Wf is tested formation sample pack width, expressed in inches.

After the baseline conductivity for each crushed formation sample was established, deionized (DI) water was then flowed through the test cell cavity and formation sample therein to remove the salt, followed by nitrogen gas which was then flowed through the cell and formation sample to remove the DI water. Next, with the crushed formation sample pack dry, the pore space in the pack of each test run was vacuum saturated in the test cell cavity with filtered Eagleford formation oil until all entrained gas was removed. The amount of oil injected into each test cell cavity during this saturation step was measured and recorded. The leak off ports remained closed during the oil injection, and each crushed formation sample pack was allowed to stand for 12 hours or overnight.

Next, each of several different designated test solutions was mixed and flowed through a corresponding one of the crushed formation sample packs in the test cell cavity for 50 hours at 500 psi applied compressional stress. These test solutions included a solution of 2% potassium chloride water with no other added chemicals, and several different types of well stimulation or enhanced oil recovery surfactants (surface active agents) mixed with 2% potassium chloride water. Each of the tested surface active agent solutions of Table 1 exhibited a different surface tension and contact angle as shown. During and after each test run, the oil and aqueous phase produced from each crushed formation sample was collected in the volumetric separator and the amount of oil produced during each flow was recorded (see Tables 1 and 2).

For the test solutions of Table 1, values of surface tension and contact angle were determined at ambient pressure and temperature (66° F. to 69.9° F.). Values of contact angle were determined using polished calcite crystal plates with an average reported roughness of 1.85 μm and using TR100 surface roughness meter and ASTM D7490-8 procedure with humidity of 70% to 71%. The calcite plates were polished with multiple polishing discs with increasing mesh number up to final polishing plate of 600 mesh. The values of surface tension were determined from average of three values using DuNouy Ring and Huh-Mason correction method.

TABLE 1

Crushed Eagleford Shale Tests
(Each test run with sample loading of 4 lb/ft² at 500 psi applied compressional stress and at 87° C. test temperature)

| Test Solution No. | Type of Fluid | Chem. Amount (gpt) | Surface Tension (mN/m) | Contact Angle (Degrees) | Sample Pack Width | Sample Cond (md-ft) | Sample Perm (Darcy) | Oil Injected (ml) | Oil Produced (ml) |
|---|---|---|---|---|---|---|---|---|---|
| 1 | Brine | KCl only | 56 | 57.99 | 0.483 | 73 | 2 | 16.9 | 2.0 |
| 2 | Blend of surfactants and solvents | 1 | 31.74 | 38.25 | 0.458 | 62 | 2 | 16.9 | 1.0 |
| 3 | polyethylene glycol monohexyl ether | 1 | 30.64 | 52.87 | 0.452 | 45 | 2 | 17 | 12.5 |
| 4 | Solvent surfactant microemulsion | 1 | 30.20 | 37.75 | 0.452 | 65 | 2 | 17 | 10.0 |
| 5 | Blend of surfactants in water | 1 | 31.51 | 35.03 | 0.467 | 68 | 2 | 17 | 6.0 |
| 6 | Methyl alcohol, ethoxylated alcohols and sodium hydroxide | 1 | 29.59 | 30.24 | 0.4725 | 58 | 1 | 17 | 3.5 |

TABLE 2

Crushed Eagleford Shale Tests
(Each test run with sample loading of 4 lb/ft² at 500 psi applied compressional stress and at 87° C. test temperature)

| Test Solution No. | Type of Fluid | Chem. Amount (gpt) | Sample Pack Width | Sample Cond (md-ft) | Sample Perm (Darcy) | Oil Injected (ml) | Oil Produced (ml) |
|---|---|---|---|---|---|---|---|
| 7 | Solvent surfactant microemulsion | 0.5 | 0.472 | 89 | 2 | 17.1 | 9.50 |
| 8 | Methyl alcohol, ethoxylated alcohols and sodium hydroxide | 2.0 | 0.451 | 76 | 2 | 17 | 7.0 |
| 9 | Blend of surfactants in water | 2.0 | 0.472 | 71 | 2 | 17 | 0.3 |

Tables 3-5 show oil production volume (in milliliters) versus time (in minutes) for each of test solutions 7, 8 and 9 of Table 2.

TABLE 3

Oil Production Volume versus Time for Test Solution 7

| minutes | mls. |
|---|---|
| 5 | 0 |
| 10 | 0.32 |
| 15 | 1.08 |
| 60 | 3.48 |
| 150 | 6.33 |
| 210 | 6.65 |
| 300 | 6.97 |
| 360 | 7.28 |
| 720 | 7.60 |
| 1440 | 8.23 |
| 3000 | 9.50 |

TABLE 4

Oil Production Volume versus Time for Test Solution 8

| minutes | mls. |
|---|---|
| 5 | 0 |
| 10 | 0.6 |
| 15 | 1 |

TABLE 4-continued

Oil Production Volume versus Time for Test Solution 8

| minutes | mls. |
|---|---|
| 60 | 3.5 |
| 150 | 4.5 |
| 210 | 5 |
| 300 | 5.5 |
| 360 | 6 |
| 720 | 6.5 |
| 1440 | 6.5 |
| 3000 | 7 |

TABLE 5

Oil Production Volume versus Time for Test Solution 9

| minutes | mls. |
|---|---|
| 5 | 0 |
| 10 | 0 |
| 15 | 0.2 |
| 60 | 0.2 |
| 150 | 0.2 |
| 210 | 0.3 |
| 300 | 0.3 |
| 360 | 0.3 |
| 720 | 0.3 |
| 1440 | 0.3 |
| 3000 | 0.3 |

Figure 3:
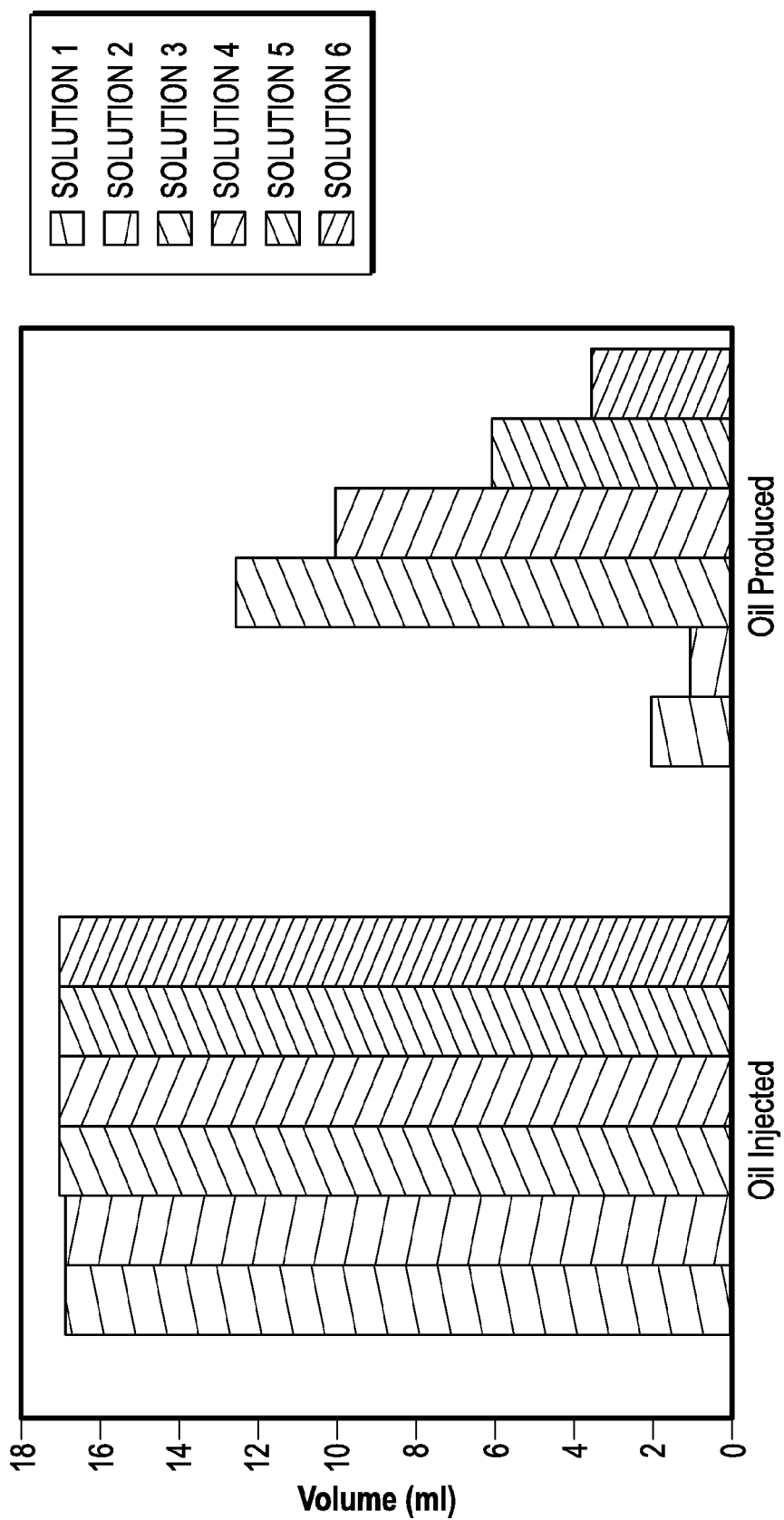
FIG. 3 is a bar graph that illustrates initial oil injection volumes and corresponding oil production volume recovered from the crushed formation samples during injection of each of respective test solutions 1-6 of Table 1 according to one exemplary embodiment of the disclosed methods and systems.
Figure 4:
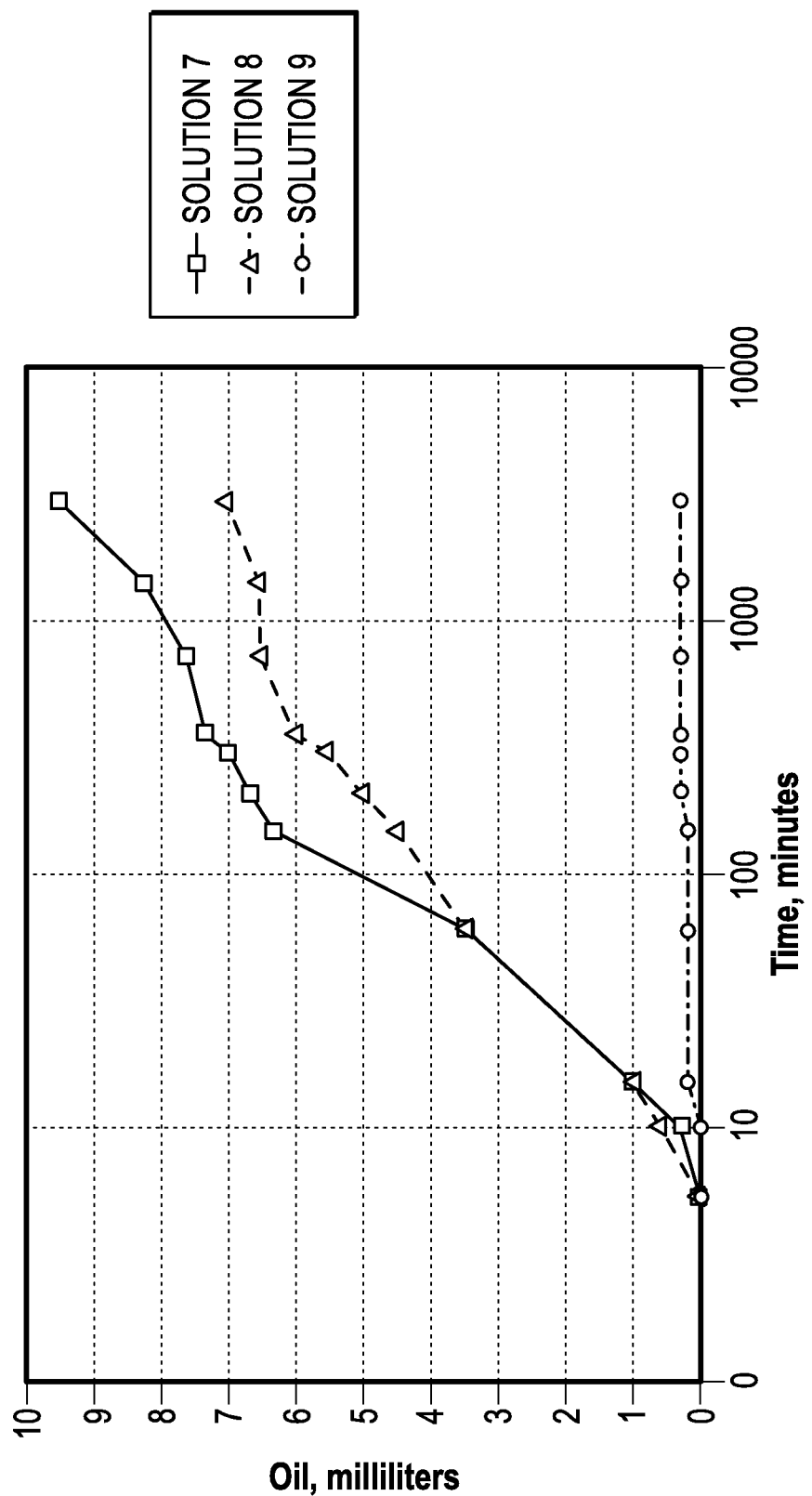
FIG. 4 graphically illustrates comparison of produced oil recovered from respective oil-saturated crushed Eagleford shale formation samples versus time during the injection of each of respective test solutions 7, 8 and 9 of Table 2 according to one exemplary embodiment of the disclosed methods and systems.

FIG. 3 is a bar graph that illustrates initial oil injection volumes required to saturate each Eagleford shale crushed formation sample and the corresponding compared oil production volume recovered from the crushed formation samples during injection of each of respective test solutions 1-6 of Table 1. FIG. 4 graphically illustrates comparison of produced oil recovered from respective oil-saturated crushed Eagleford shale formation samples versus time during the injection of each of respective test solutions 7, 8 and 9 of Table 2.

While the invention may be adaptable to various modifications and alternative forms, specific examples and exemplary embodiments have been shown by way of example and described herein. However, it should be understood that the invention is not intended to be limited to the particular forms disclosed. Rather, the invention is to cover all modifications, equivalents, and alternatives falling within the spirit and scope of the methods and systems described herein. Moreover, the different aspects of the disclosed methods and systems may be utilized in various combinations and/or independently. Thus the invention is not limited to only those combinations shown herein, but rather may include other combinations.

What is claimed is:

1. A method, comprising:
substantially saturating the pore spaces of a crushed formation sample with hydrocarbon;
applying a compressional stress to the saturated crushed formation sample;
flowing a test solution through the crushed formation sample while the crushed formation sample is subjected to the applied compressional stress to produce an effluent from the crushed formation sample; and
determining the amount of hydrocarbon recovered from the effluent produced from the crushed formation sample while the crushed formation sample is subjected to the applied compressional stress.

2. The method of claim 1, where the formation has a matrix absolute permeability of less than or equal to 1 millidarcies (md).

3. The method of claim 1, where the formation has a matrix absolute permeability of from 0.001 md to 1 md.

4. The method of claim 1, where the crushed formation sample comprises at least one of shale, limestone, or a combination thereof.

5. The method of claim 1, where the crushed formation sample comprises shale.

6. The method of claim 1, where the hydrocarbon comprises oil.

7. The method of claim 1, further comprising:
substantially saturating the pore spaces of a crushed formation sample with hydrocarbon produced from the formation under reservoir conditions;
applying a compressional stress to the saturated crushed formation sample that is substantially equivalent to an in situ downhole overburden stress corresponding to the reservoir conditions for the formation material;
flowing the test solution through the crushed formation sample to produce the effluent from the crushed formation sample while the crushed formation sample is subjected to the applied compressional stress that is substantially equivalent to an in situ overburden stress corresponding to the reservoir conditions for the formation material; and
determining the amount of hydrocarbon recovered from the effluent produced from the crushed formation sample.

8. The method of claim 7, further comprising flowing the test solution through the crushed formation sample while the crushed formation sample is subjected to a temperature that is substantially equivalent to an in situ downhole temperature corresponding to the reservoir conditions for the formation material.

9. The method of claim 1, where the test solution comprises at least one surface active agent.

10. The method of claim 1, further comprising:
substantially saturating the pore spaces of multiple crushed formation samples with hydrocarbon;
applying a compressional stress to each of the saturated crushed formation samples;
flowing a different test solution through each given one of the crushed formation samples while the given crushed formation sample is subjected to the applied compressional stress to produce an effluent from each of the given crushed formation sample that corresponds to a different one of the test solutions; and
determining the amount of hydrocarbon recovered from the effluent corresponding to each one of the different test solutions.

11. The method of claim 1, where the crushed formation sample has a first end and a second end opposite from the first end, and where the method further comprises:
positioning the crushed formation sample into a test cell cavity of a conductivity test cell body of a conductivity cell apparatus between two pistons, and with the first end of the crushed formation sample being disposed adjacent a fluid inlet to the test cell cavity and the second end of the crushed formation sample being disposed adjacent a fluid outlet from the test cell cavity;
using the pistons to apply the compressional stress to the saturated crushed formation sample within the test cell cavity;
introducing the test solution into the fluid inlet of the test cell cavity to induce flow of the test solution through the crushed formation sample from the first end of the crushed formation sample to the second end of the crushed formation sample while the crushed formation sample is subjected to the applied compressional stress to produce an effluent from the crushed formation sample that outflows from the fluid outlet of the test cell cavity; and determining the amount of hydrocarbon recovered from the effluent produced from the crushed formation sample.

12. The method of claim 11, where the hydrocarbon comprises oil.

13. The method of claim 12, further comprising:

positioning a respective permeable compression die between each of the two pistons and the crushed formation sample; and saturating each of the permeable compression dies with oil prior to introducing the test solution into the fluid inlet of the test cell cavity to induce flow of the test solution through the crushed formation sample to produce the effluent from the crushed formation sample.

14. The method of claim 11, where the test solution is an aqueous-based test solution; and where the method further comprises receiving the effluent from the fluid outlet of the test cell cavity in a volumetric separator; and measuring an amount of hydrocarbon that is separated from an aqueous phase within the volumetric separator.

15. The method of claim 11, where the applied compressional stress is from 250 psi to 20,000 psi.

16. The method of claim 11, where the applied compressional stress is from 50 psi to 20,000 psi.

17. The method of claim 11, where the applied compressional stress is greater than 20,000 psi.

18. The method of claim 1, where the crushed formation sample has a first end and a second end opposite from the first end, and where the method further comprises:

positioning the crushed formation sample into a test cavity defined within a first end of a flow-through test cell system body between a movable piston and a stationary end cap, with the first end of the crushed formation sample being disposed adjacent at least one opening that is defined to extend through the movable piston to the test cell cavity and the second end of the crushed formation sample being disposed adjacent at least one fluid outlet that is defined in the stationary end cap of the flow-through test cell;

introducing a pressure application fluid into a closed pressure application cavity defined within a second end of the system body to cause an increase in fluid pressure differential across the movable piston between the closed pressure application cavity and the test cell cavity to apply the compressional stress to the saturated crushed formation sample within the test cell cavity;

introducing the test solution into the test cell cavity through the opening defined in the movable piston to induce flow of the test solution through the crushed formation sample from the first end of the crushed formation sample to the second end of the crushed formation sample while the crushed formation sample is subjected to the applied compressional stress due to the fluid pressure differential across the movable piston to produce an effluent from the crushed formation sample that outflows from the fluid outlet of the test cell cavity; and determining the amount of hydrocarbon recovered from the effluent produced from the crushed formation sample.

19. The method of claim 1, where the formation has a matrix absolute permeability of less than 0.001 md.

20. The method of claim 1, where the formation has a matrix absolute permeability of greater than 1 md.

21. A test system, comprising:

a system body having a test cavity defined therein that contains a crushed formation sample that is substantially saturated with hydrocarbon;

at least one fluid inlet in fluid communication with the test cavity and configured to receive a test solution to induce a flow of fluid through the crushed formation sample to produce an effluent;

at least one fluid outlet in fluid communication with the test cavity and configured to receive the effluent from the crushed formation sample; and at least one stress application member configured to apply compressive stress to the saturated sample of crushed formation material contained within the test cavity at the same time that fluid flow is induced through the crushed formation sample from the fluid inlet to the fluid outlet of the test cavity;

where a fluid seal is formed around the crushed formation sample within the test cavity to substantially contain pressurized fluid flow through the crushed formation sample from the fluid inlet to the fluid outlet.

22. The test system of claim 21, further comprising a fluid measurement apparatus coupled to the fluid outlet of the test cavity, the fluid measurement apparatus being configured to measure the volume or relative volume of hydrocarbon fluid relative to aqueous phase fluid contained in the effluent received from the fluid outlet of the test cavity during induced fluid flow through the crushed formation sample.

23. The test system of claim 22, where the fluid measurement apparatus comprises a volumetric separator.

24. The test system of claim 21, where the at least one stress application member comprises two pistons; where the saturated crushed formation sample is disposed within the test cavity between the two pistons, the two pistons being configured move toward each other so as to cooperatively provide an inward compression force to the saturated sample of crushed formation material.

25. The test system of claim 24, where the saturated crushed formation sample has a first end and a second end opposite from the first end; where the saturated crushed formation sample is disposed within the test cavity between the two pistons with the first end of the saturated crushed formation sample being disposed adjacent the fluid inlet to the test cavity and the second end of the saturated crushed formation sample being disposed adjacent the fluid outlet from the test cavity; and where the test system further comprises a respective permeable compression die positioned between each of the two pistons and the crushed formation sample, each of the permeable compression die being saturated with hydrocarbon.

26. The test system of claim 21, where the formation has a matrix absolute permeability of less than or equal to 1 millidarcies (md); and where the crushed formation sample comprises at least one of shale, limestone, or a combination thereof.

27. The test system of claim 21, where the formation has a matrix absolute permeability of greater than 1 md; and where the crushed formation sample comprises at least one of shale, limestone, or a combination thereof.

28. A test system, comprising:

a system body having a test cavity defined within a first end of the system body and a closed pressure application cavity defined within a second end of the system body, the test cavity being sealed from the closed pressure application cavity such that an internal volume of the test cavity has substantially no fluid communication with an internal volume of the closed pressure application cavity, and the test cavity being configured to receive a crushed formation sample therein;

a movable piston sealingly received within the system body between the first and second ends of the system body, the movable piston being movable between the first and second ends of the system body while at the same time maintaining a fluid seal between the test cavity and the closed pressure application cavity;

a movable inlet fluid conduit extending from outside the second end of the system body through the closed pressure application cavity and through an opening defined in the movable piston, the inlet fluid conduit forming a fluid seal with the system body and having substantially no fluid communication with the closed pressure application cavity;

at least one system fluid inlet in fluid communication with the inlet fluid conduit such that the system fluid inlet is in fluid communication with the test cavity, the system fluid inlet and test fluid conduit being configured to receive a first injected fluid to induce a flow of fluid through the crushed formation sample to produce an effluent;

at least one pressure application fluid inlet in communication with the closed pressure application cavity and configured to receive a pressure application fluid that is injected into the closed pressure application cavity to cause an increase in fluid pressure differential across the movable piston between the closed pressure application cavity and the test cavity; and at least one fluid outlet in fluid communication with the test cavity and configured to receive the effluent from the crushed formation sample;

where the movable piston is configured to respond to an increase in fluid pressure differential between the closed pressure application cavity and the test cavity by applying compressive stress to the crushed formation material contained within the test cavity at the same time that injection of the first fluid induces fluid flow through the crushed formation sample from the system fluid inlet to the fluid outlet of the test cavity.

* * * * *